Figure 2:
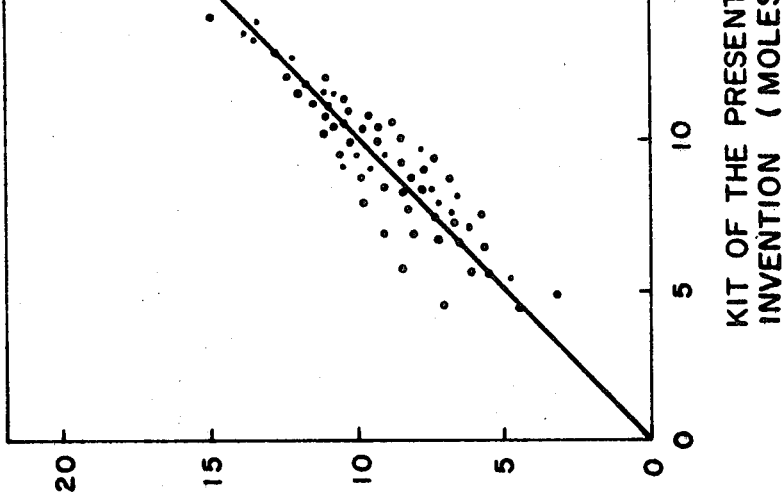

United States Patent [19]

Yamaguchi et al.

[11] 4,367,285
[45] Jan. 4, 1983

[54] ASSAYING LIPID PEROXIDE IN LIPID COMPOSITIONS

[75] Inventors: Tsutomu Yamaguchi, Yamaguchi; Hideo Misaki, Shizuoka, both of Japan

[73] Assignee: Toyo Jozo Company, Ltd., Tokyo, Japan

[21] Appl. No.: 234,668

[22] Filed: Feb. 17, 1981

[30] Foreign Application Priority Data

Feb. 21, 1980 [JP] Japan ................. 55-021220

[51] Int. Cl.³ ............... G01N 33/52; G01N 33/92
[52] U.S. Cl. .................................. 435/28; 422/61; 435/810; 436/71
[58] Field of Search ............ 435/28, 810; 422/61; 23/909

[56] References Cited

U.S. PATENT DOCUMENTS

| | | | |
|---|---|---|---|
| 3,979,262 | 9/1976 | Hunziker | 435/28 X |
| 4,251,629 | 2/1981 | Yamanisi | 435/28 |
| 4,260,393 | 4/1981 | Gibson | 435/28 X |
| 4,260,679 | 4/1981 | Tsuda | 23/909 X |
| 4,273,868 | 6/1981 | Walter | 435/28 X |
| 4,295,853 | 10/1981 | Kasahara | 23/909 X |

FOREIGN PATENT DOCUMENTS 56-21600 2/1981 Japan .
56-48104 4/1981 Japan ................................... 23/909

OTHER PUBLICATIONS

D. H. Wheeler, Oil and Soap, 9, 89–97 (1932).
C. M. Stine et al., J. Dairy Sci, 37, 202–208 (1954).
A. L. Tappel et al., Arch. Biochem. Biophys., 80, 326–332 (1959).
"The Enzymes," Paul D. Boyer et al., Eds., Chapt. 7, by K. G. Paul, Academic Press, New York, 1963.

*Primary Examiner*—Sidney Marantz
*Attorney, Agent, or Firm*—Wyatt, Gerber, Shoup, Scobey & Badie

[57] ABSTRACT

Method and kit for measuring lipid peroxides is provided, in which the measuring reagent contains peroxidase and a hydrogen donor. The method can be used to determine the amount of lipid peroxides in foods or body fluids.

5 Claims, 2 Drawing Figures

ASSAYING LIPID PEROXIDE IN LIPID COMPOSITIONS

The present invention pertains to a kit for measuring lipid peroxides, using a measuring reagent containing peroxidase and a hydrogen donor.

Lipid peroxides are peroxides of lipids, including fatty acids. They have been implicated recently in such problems as aging, atheroscrelosis, carcinogenicity, etc. Accordingly, facile and precise measurement of lipid peroxides in foods, such as convenience foods, margarine, butter, etc. and body fluids, such as serum, urine, etc., is very important from the viewpoints of food safety, and the prophylaxis, diagnosis and therapy of diseases.

Previously known methods for measuring lipid peroxides, include the Wheeler method, iron thiocyanate method, thiobarbituric acid method, and others. These methods have their own, merits and demerits, and do not accomplish the objects mentioned above with complete satisfaction. The Wheeler method [D. H. Wheeler: Oil and Soap, 9, 89–97 (1932)] is that in which lipid peroxide is reacted with potassium iodide to isolate iodine, which is then titrated with a sodium thiosulfate standard solution. The difficulties of this measurement are in a large amount of chloroform and acetic acid required as the organic solvent, the large amount of rather expensive reagents, such as potassium iodide, required the large amount of the sample which may be as high as 5 to 10 g. needed in the case of a sample of a low peroxide value, the complicated operation due to the titration, and the fact that its sensitivity is inferior to the other methods. In the iron thiocyanate method [C. M. Stine, H. A. Harland, S. T. Caulter and R. Jeness; J. Dairy Sci., 37, 202 (1954)] lipid peroxide is mixed with ammonium thiocyanate and ferrous chloride, and the blue color from the resulting iron thiocyanate is colorimetrically determined. Although the sensitivity of the method is high, this method is disadvantageous in that the colorimetry must be conducted no later than 3 minutes after mixing, since the color tends to fade rapidly, the somewhat inferior accuracy, the high degree of skill required, the time and the labor necessitated to decide the dilution ratio due to the narrow measuring range, and others. In the thiobarbituric acid method [A. L. Tappel and H. Zalkin; Arch. Biochem. Biophys., 80, 326 (1959)] the lipid peroxide is heated under acidic conditions and the resulting malondialdehyde is condensed with thiobarbituric acid to form a red color dye, which is then colorimetrically measured. Although the sensitivity is excellent, the disadvantages of this method are, among others, that if the sample contains an aldehyde other than malondialdehyde, glucose, and the like, it does not give an accurate value, since they also contribute to the color, that the measuring range of this method is narrow, and that peroxides which do not yield malondialdehyde under acidic conditions can not be measured. Recently, enzymatic measurements in which various constituents in the sample, including body fluids, are easily and accurately measured, utilizing enzyme specificity, have been employed for clinical diagnosis. In previously known chemical analyses, if only the objective compound in a sample containing a number of similar compounds is to be measured it was necessary to separate the objective compound from the other constituents as far as possible before analysis. Otherwise, an accurate value could not be obtained. In enzymatic methods utilizing enzyme specificity, however, direct measurement of the objective compound without separation from other analogous compounds is possible by use of an enzyme which acts exclusively on the objective compound.

For instance, uric acid, glucose, neutral fats, cholesterol, creatine, hydrogen peroxide, etc. have come been measured easily and accurately by use of the enzymatic method.

For the assay of hydrogen peroxide, horseradish peroxidase has been employed in the enzymatic methods. Detailed investigations have been made by a number of researchers on horseradish peroxidase.

Paul et al reported that horseradish peroxidase has extremely high substrate specificity, and that the compounds subjected to enzymatic action with horseradish peroxidase are confined to three kinds of peroxides, namely of dihydrogen peroxide ($H_2O_2$, hydrogen peroxide), monomethylhydrogen peroxide ($CH_3OOH$) and monoethylhydrogen peroxide ($C_2H_5OOH$) [K. G. Paul; The Enzyme 8, 227 (1963)].

For measuring lipid peroxides, however, such enzymatic measuring methods have not been proposed, since no enzyme has so far been known which acts on these compounds. Thus, the chemical methods of analysis as mentioned above with their known difficulties were necessarily used for the measurement of lipid peroxides.

It has now been found that peroxidase unexpectedly decomposes lipid peroxides and that the resulting reaction system colors intensely with increasing quantities of lipid peroxide, if an adequate hydrogen donor is present in the reaction system.

Thus, one embodiment of the present invention is a measuring kit for lipid peroxidase containing peroxidase and a hydrogen donor.

Figure 1:
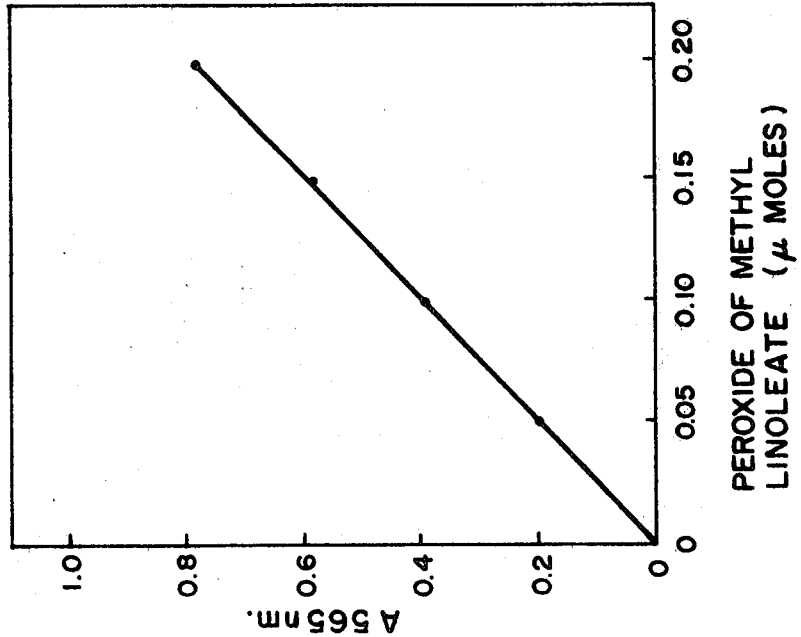

In the accompanying drawings,

FIG. 1 is a graph showing the direct relationship between the amount of methyl linoleate peroxide and the extinction coefficient, and FIG. 2 is a graph showing a correlation of human serum lipid peroxide quantification between the kit of the present invention and a commercially available kit.

The peroxidase employed in the present invention is preferably any of the commercially available horseradish peroxidases, which normally contain not less than 1 unit (1 U hereinafter) per test, preferably about 1.5 to 5 units.

The hydrogen donor employed in the present invention is any of the known oxidizable compounds which, preferably, generate color, fluorescence or luminescence upon oxidation. The conventional coloring, fluorescent, luminescent reagents may be utilized. Amongst the known coloring reagents which may be employed, there may be mentioned, for example, guaiacol, 4-aminoantipyrine with phenol, 4-aminoantipyrine with N,N-dimethylaniline, 3-methyl-2-benzothiazolinone with dimethylaniline, ortho-dianisidine, and the like. Typically useful fluorescent reagents include homovanillic acid, p-hydroxyphenylacetic acid, and the like. As luminescent reagents, luminol and the like may be mentioned by way of illustration. All of these reagents are mentioned merely for exemplification, and not for limitation, of the hydrogen donor of the present invention.

The amount of the hydrogen donor employed is at least equimolar, preferably not less than two moles, per mole of lipid peroxide contained in test sample. The amount may be varied depending upon the size of the sample and the content of the lipid peroxide in the sample.

Suitable reaction mediums which may be employed include dimethylglutarate-sodium hydroxide buffer solution, phosphate buffer solution and, Tris-hydrochloric acid buffer solution is normally from 5 to 9.

A typical measuring kit (3 ml) may contain a 50 mM dimethylglutarate-sodium hydroxide buffer solution (pH 6.0) containing 0.03% (W/V) of 4-aminoantipyrine, 0.04% (V/V) of N,N-dimethylaniline and 4.5 units of peroxidase. In a typical measurement, the kit is preliminarily warmed to 37° C. and 50 μl of a test sample containing lipid peroxide is added. The mixture is incubated at 37° C. for 15 minutes and, the intensity of the color generated is measured suing a spectrophotometer at a wavelength of, for example, 565 nm. The amount of the lipid peroxide in the sample is calculated from the extinction value.

The reaction according to the present invention is presumed to be based on the following equation:

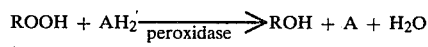

$$ROOH + AH_2 \xrightarrow{peroxidase} ROH + A + H_2O$$

wherein R represents a lipid residue and $AH_2$ represents a hydrogen donor. Linoleic acid contained in foods and other materials yields two kinds of lipid peroxides, namely, 9-hydroperoxy-10,12-octadecadienoic acid and/or 13-hydroperoxy-9,11-octadecadienoic acid. These peroxides can be measured according to the present invention.

In the practice of the present invention, such factors as the pH at the time of reaction, the reaction period, the measuring wavelength, etc., may be varied depending upon the reagent employed. Suitable conditions can be selected according to the circumstances.

The following non-limiting examples are given by way of illustration.

EXAMPLE 1

A measuring kit, containing 3.0 ml. of 50 mM dimethylglutarate-sodium hydroxide buffer solution (pH 6.0) containing 0.03% (W/V) of 4-aminoantipyrine, 0.04% (V/V) of N,N-dimethylaniline, and 5.0 units of peroxidase (from horseradish; purchased from Sigma Chemical Co. 100 U/mg.), was prepared.

Separate 3.0 ml. in test tubes were warmed to 37° C. for 5 minutes. Separate 50 μl. samples of an isopropanol solution containing 0 to 4 μ moles/ml. of the peroxide of methyl linoleate (95% purity, 5850 mg./Kg. peroxide value; measured by Wheeler method) were added to the separate test tubes. Each mixture was allowed to react at 37° C. for 15 minutes, and the intensity of the color generated was measured by a spectrophotometer at 565 nm.

The results are shown in FIG. 1, in which the graph shows the direct relationship between the amount of the peroxide of methyl linoleate and extinction. The results were excellent.

EXAMPLE 2

A measuring kit, containing 3.0 ml. of 100 mM phosphate buffer solution (pH 7.0) containing 0.01% (W/V) of homovanillic acid and 5.0 units of horseradish peroxidase, was prepared.

To this measuring kit solution was added 50 μl. of human serum, and the mixture was allowed to react at 37° C. for 15 minutes. Thereafter, the intensity of fluorescence was measured with an Hitachi's fluorospectrophotometer at 315 nm excitation wavelength and 425 nm emission wavelength, to determine the correlation with the measured values from a commercial kit (thiobarbituric acid method; manufactured by Wako Pure Chemicals Co. Ltd.).

A blank test was carried out by a similar procedure, using a reaction medium from which peroxidase had been omitted.

The results are shown in FIG. 2, which shows an excellent correlation of human serum lipid peroxide quantification between the kit of the present invention and the commercially available kit.

Correlation coefficient: $\gamma = 0.934$, $Y = 0.93x - 0.2$, $n = 48$.

We claim:

1. A process of assaying the presence of lipid peroxide in lipid compositions comprising the steps of:
   A. Contacting a sample of the lipid composition, in the presence of an oxidizable hydrogen donor with a peroxidase enzyme at a temperature of about 37° C. at a pH of from about 5 to 9 to develop a color, fluorescence or luminescence, said oxidizable hydrogen donor being present in a molar concentration at least equal to the molar concentration of the lipid peroxide;
   B. Detecting resulting color, fluorescence or luminescence; and
   C. Correlating the result of Step B with the presence of lipid peroxide in the lipid composition.

2. A process as in claim 1 wherein the hydrogen donor generates color and is selected from the group consisting of guaiacol, 4-aminoantipyrine with phenol, 4-methyl-2-benzothiazolinone with N,N-dimethylaniline and ortho-dianisidine.

3. A process as in claim 1 wherein the hydrogen donor generates fluorescence and is selected from the group consisting of homovanillic acid and p-hydrophenylacetic acid.

4. A process as in claim 1 wherein the hydrogen donor is luminol.

5. A process as in claim 1 wherein the molar concentration of hydrogen donor is not less than two times the molar concentration of lipid peroxide.

* * * * *